United States Patent
Singh et al.

(10) Patent No.: US 8,815,295 B1
(45) Date of Patent: Aug. 26, 2014

(54) ANTI RESPIRATORY SYNCYTIAL VIRUS PEPTIDE FUNCTIONALIZED GOLD NANOPARTICLES

(71) Applicants: Shree R. Singh, Montgomery, AL (US); Pooja M. Tiwari, Montgomery, AL (US); Vida A. Dennis, Montgomery, AL (US)

(72) Inventors: Shree R. Singh, Montgomery, AL (US); Pooja M. Tiwari, Montgomery, AL (US); Vida A. Dennis, Montgomery, AL (US)

(73) Assignee: Alabama State University, Montgomery, AL (US)

( * ) Notice: Subject to any disclaimer, the term of this patent is extended or adjusted under 35 U.S.C. 154(b) by 0 days.

(21) Appl. No.: 13/722,517

(22) Filed: Dec. 20, 2012

Related U.S. Application Data

(60) Provisional application No. 61/578,883, filed on Dec. 22, 2011.

(51) Int. Cl.
| | |
|---|---|
| *A61K 9/16* | (2006.01) |
| *A61K 9/50* | (2006.01) |
| *A01N 37/18* | (2006.01) |
| *A61K 38/00* | (2006.01) |
| *A61P 31/12* | (2006.01) |
| *A61K 38/16* | (2006.01) |
| *C07K 14/135* | (2006.01) |

(52) U.S. Cl.
CPC ............... *C07K 14/135* (2013.01); *A61K 38/16* (2013.01); *A61K 9/16* (2013.01); *A61K 9/50* (2013.01)
USPC ............................ 424/491; 514/21.3; 514/3.7

(58) Field of Classification Search
None
See application file for complete search history.

(56) References Cited

U.S. PATENT DOCUMENTS

| | | | |
|---|---|---|---|
| 5,852,015 | A | 12/1998 | Gluzman et al. |
| 6,855,493 | B2 | 2/2005 | Young et al. |
| 7,186,274 | B2 | 3/2007 | Vic et al. |
| 7,700,720 | B2 | 4/2010 | Tous et al. |
| 8,241,393 | B2 | 8/2012 | Raghuraman et al. |
| 8,304,257 | B2 | 11/2012 | Ackerson et al. |
| 8,309,135 | B2 | 11/2012 | Chen et al. |
| 2006/0099220 | A1 | 5/2006 | Tous et al. |
| 2010/0261155 | A1 | 10/2010 | Peeples et al. |
| 2011/0166061 | A1 | 7/2011 | Erickson et al. |

OTHER PUBLICATIONS

Wolf et al "A broad-spectrum antiviral targeting entry of enveloped viruses" Proc Nat Acad Sci 107:3157-3162. Published Feb. 16, 2010.*
Anonymous "Respiratory Syncytial Virus Infection (RSV)" Centers for Disease Control and Prevention website. <http://cdc.gov/rsv/about/transmission.html> Accessed on the Internet Sep. 26, 2013.*

* cited by examiner

*Primary Examiner* — Maury Audet
*Assistant Examiner* — Zachary J Miknis
(74) *Attorney, Agent, or Firm* — Bush Intellectual Property Law; Kenneth M. Bush

(57) ABSTRACT

Anti-RSV peptide and a segment thereof derived from a peptide sequence identified in the human RSV fusion protein precursor F0. Another anti-RSV agent is carboxylated gold nanoparticles. A method is provided for attaching peptides to the carboxylated gold particles to produce additional anti-RSV agents to prevent or inhibit infection by the respiratory syncytial virus (RSV) and related viruses, including the human immunodeficiency virus (HIV).

12 Claims, 7 Drawing Sheets

RF482 VFPSDEFDASISQVNEKINQSLAFIRKSDLLHNVNAGKK
RF491 SISQVNEKINQSLAFIRKSD

SEQUENCE LISTING

<160> NUMBER OF SEQ ID NOS: 2

<210> SEQ ID NO 1
<211> LENGTH: 39
<212> TYPE: PRT
<213> ORGANISM: respiratory syncytial virus

<400> SEQUENCE: 1

Val Phe Pro Ser Asp Glu Phe Asp Ala Ser Ile Ser Gln Val Asn Glu
1               5                   10                  15

Lys Ile Asn Gln Ser Leu Ala Phe Ile Arg Lys Ser Asp Leu Leu His
            20                  25                  30

Asn Val Asn Ala Gly Lys Lys
        35

<210> SEQ ID NO 2
<211> LENGTH: 20
<212> TYPE: PRT
<213> ORGANISM: respiratory syncytial virus

<400> SEQUENCE: 2

Ser Ile Ser Gln Val Asn Glu Lys Ile Asn Gln Ser Leu Ala Phe Ile
1               5                   10                  15

Arg Lys Ser Asp
            20

ANTI RESPIRATORY SYNCYTIAL VIRUS PEPTIDE FUNCTIONALIZED GOLD NANOPARTICLES

CROSS-REFERENCE TO RELATED APPLICATIONS

This application claims priority to U.S. Provisional Patent Application No. 61/578,883, filed Dec. 22, 2011, which is incorporated herein by reference in its entirety.

STATEMENT REGARDING FEDERALLY SPONSORED RESEARCH

This invention was supported in whole or in part with government support by grant number NSF-CREST (HRD-1241701) from the National Science Foundation.

FIELD OF THE INVENTION

The present invention relates to pharmaceutical compositions comprising an anti-RSV-F peptide segment (exemplified by SEQ ID NO.:1) from the respiratory syncytial virus (RSV) F protein precursor F0 wherein the anti-RSV-F peptide is linked to gold nanoparticles, particularly to gold nanoparticles having a carboxyl polymer coating. This invention further includes the anti-RSV-F peptide, carboxylated gold nanoparticles, and the anti-RSV-F peptide conjugated to the carboxylated gold nanoparticles as pharmacologic agents for preventing, treating or ameliorating symptoms associated with RSV infection, wherein these methods comprise administering to a human subject an effective amount of one or more of these pharmacologic agents to effectively prevent or treat RSV infection.

BACKGROUND OF THE INVENTION

Human respiratory syncytial virus (RSV) belongs to the Pneumovirus subfamily of the Paramyxoviridae family with a negative single strand RNA genome and enveloped nucleocapsid (Respiratory Syncytial Virus—Human Paramyxoviridae, Encyclopedia of Virology, Second Edition, G. Allan and G. W. Robert, Eds Oxford, Elsevier, pp. 1479-1487). RSV is the leading cause of pediatric bronchiolitis, pneumonia, and bronchitis worldwide and is also a significant cause of morbidity and mortality in the elderly. Respiratory syncytial virus (RSV) is the leading cause of serious lower respiratory tract disease in infants and children (Feigen et al., eds., 1987, In: Textbook of Pediatric Infectious Diseases, W B Saunders, Philadelphia at pages 1653-1675; New Vaccine Development, Establishing Priorities, Vol. 1, 1985, National Academy Press, Washington D.C. at pages 397-409; and Ruuskanen et al., 1993, Curr. Probl. Pediatr. 23:50-79). The yearly epidemic nature of RSV infection is evident worldwide (Hall, C. B., 1993, Contemp. Pediatr. 10:92-110). Primary RSV infection occurs most often in children from 6 weeks to 2 years of age and uncommonly in the first 4 weeks of life during nosocomial epidemics (Hall et al., 1979, New Engl. J. Med. 300: 393-396). Children at increased risk from RSV infection include preterm infants (Hall et al., 1979, New Engl. J. Med. 300:393-396) and children with bronchopulmonary dysplasia (Groothuis et al., 1988, Pediatrics 82:199-203), congenital heart disease (MacDonald et al., New Engl. J. Med. 307:397-400), congenital or acquired immunodeficiency (Ogra et al., 1988, Pediatr. Infect. Dis. J. 7:246-249; and Pohl et al., 1992, J. Infect. Dis. 165:166-169), and cystic fibrosis (Abman et al., 1988, J. Pediatr. 113:826-830). The fatality rate in infants with heart or lung disease who are hospitalized with RSV infection is 3%-4% (Navas et al., 1992, J. Pediatr. 121:348-354).

RSV infects adults as well as infants and children. In healthy adults, RSV causes predominantly upper respiratory tract disease. It has recently become evident that some adults, especially the elderly, have symptomatic RSV infections more frequently than had been previously reported (Evans, A. S., eds., 1989, Viral Infections of Humans. Epidemiology and Control, 3.sup.rd ed., Plenum Medical Book, New York at pages 525-544). Several epidemics also have been reported among nursing home patients and institutionalized young adults (Falsey, A. R., 1991, Infect. Control Hosp. Epidemiol. 12:602-608; and Garvie et al., 1980, Br. Med. J. 281:1253-1254). RSV also may cause serious disease in immunosuppressed persons, particularly bone marrow transplant patients (Hertz et al., 1989, Medicine 68:269-281).

Viral and host factors in human RSV pathogenesis are known (J Virol 82(5): 2040-2055). Two glycoproteins, F and G, on the surface of RSV have been shown to be targets of neutralizing antibodies (Fields et al., 1990, supra; and Murphy et al., 1994, supra). These two proteins are also primarily responsible for viral recognition and entry into target cells; G protein binds to a specific cellular receptor and the F protein promotes fusion of the virus with the cell. The F protein is also expressed on the surface of infected cells and is responsible for subsequent fusion with other cells leading to syncytia formation. Thus, antibodies to the F protein, or other inhibitors of the F protein, may directly neutralize virus or block entry of the virus into the cell or prevent syncytia formation. However, the manufacturing of antibodies is very expensive and the amount of antibody that can be purified and concentrated is limited. To date, no effective vaccine has been developed against RSV due to the lack of suitable animal models and to various immunological obstacles (Crowe Jr, J. E., 2001, Respiratory syncytial virus vaccine development, Vaccine 20, Supplement 1(0): S32-S37). Effective therapeutics and methodologies to eliminate human RSV infection at an early stage are needed. In addition, there is a need to inhibit the fusion process in order to proactively prevent an RSV infection.

SUMMARY OF THE INVENTION

This invention provides an anti-RSV peptide consisting of an amino acid sequence, wherein the amino acid sequence has the following structure: VFPSDEFDASISQVNEKINQS-LAFIRKSDLLHNVNAGKK (SEQ ID No: 1). This anti-RSV peptide (RF482) may be conjugated to [(2-amino-ethoxy)-ethoxy]-acetic acid (H-AEEAc) at the N-terminal of the anti-RSV peptide. The anti-RSV peptide may then be conjugated to a carboxylated gold nanoparticle at the 2-amino-end of the [(2-amino-ethoxy)-ethoxy]-acetic acid. The invention includes pharmaceutical compositions of the anti-RSV peptide, or the anti-RSV peptide conjugated to a carboxylated gold nanoparticle, and a pharmaceutically acceptable carrier or excipient, wherein the pharmaceutical composition prevents infection by a virus when administered to a subject in need thereof, preferably, a respiratory syncytial virus (RSV). The invention further includes an anti-RSV peptide consisting of an amino acid sequence, wherein the amino acid sequence has the following structure: SISQVNEKINQSLAFIRKSD (SEQ ID No: 2), wherein the anti-RSV peptide (RF491) is conjugated to (H-AEEAc) at the N-terminal of the anti-RSV peptide, and wherein the anti-RSV peptide is conjugated to a carboxylated gold nanoparticle at the 2-amino end of H-AEEAc. The invention further includes a pharmaceutical composition comprising the anti-RSV peptide of SEQ ID No: 2 conjugated to the carboxylated gold nanoparticle and a pharmaceutically acceptable carrier or excipient, wherein the pharmaceutical composition prevents infection by a virus when administered to a subject in need thereof, preferably a respiratory syncytial virus. The invention further includes a mixture of the anti-RSV peptide RF482 conjugated to the carboxylated gold nanoparticles and the anti-RSV peptide RF491 conjugated to the carboxylated gold nanoparticles, and pharmaceutically effective compositions thereof.

The invention provides a method of attaching peptides to carboxylated gold nanoparticles. The steps of the method include providing carboxylated gold nanoparticles in an aqueous solution; providing at least one peptide linked to H-AEEAc in an aqueous solution; forming a mixture of the aqueous solution of carboxylated gold nanoparticles and the aqueous solution of peptides; adding 1-ethyl-3-(3-dimethylaminopropyl) carbodiimide in water to the mixture, thereby forming carboxylated gold nanoparticles with the peptides conjugated thereto. The method may further comprise centrifuging the mixture to form a pellet; removing the supernatant resulting from the centrifuging, resuspending the pellet in water, and centrifuging. The latter step may be performed repeatedly as needed.

The invention includes a method of use of the carboxylated gold nanoparticles, made of gold salts and coated with a carboxyl polymer, for preventing or inhibiting infection by a virus, preferably the respiratory syncytial virus. The method includes the steps of 1) providing the carboxylated gold nanoparticles alone; and 2) administering the carboxylated gold nanoparticles to a subject in need thereof. The method further comprises the carboxylated gold nanoparticles being provided in a pharmaceutical composition formed of the carboxylated gold nanoparticles and a pharmaceutically acceptable carrier or excipient.

An advantage of the present invention is anti-RSV carboxylated gold nanoparticles conjugated with the peptide of SEQ ID No: 1 or with the peptide of SEQ ID No: 2, wherein these peptides are linked to H-AEEAc.

Another advantage is a water soluble small peptide which inhibits infection by the respiratory syncytial virus.

Another advantage is a simple method for linking peptides to carboxylated gold nanoparticles.

Another advantage is water soluble unconjugated carboxylated gold nanoparticles which, alone, inhibit infection by the respiratory syncytial virus.

Another advantage is anti-RSV agents that are useful prophylactically to prevent infection by the respiratory syncytial virus, including unconjugated carboxylated gold nanoparticles.

BRIEF DESCRIPTION OF THE DRAWINGS

FIG. 1 presents a schematic illustration of the binding and fusion of the RSV to cells to cause infection of the cells.

FIG. 2 presents a schematic illustration of the inhibition of RSV fusion to the cell by binding of an anti-RSV-F agent to the RSV F protein.

FIG. 3 shows the amino acid regions of the RSV fusion protein precursor F0 from which the two peptides RF482 (SEQ ID NO.:1) and RF491 (SEQ ID NO.:2) are derived.

FIG. 4 shows the Swiss model of RF482 as predicted using ProtParam.

FIG. 5 shows the interaction of RF482 with human RSV F using Hex server (protein docking software).

DETAILED DESCRIPTION OF THE INVENTION

Figure 6:
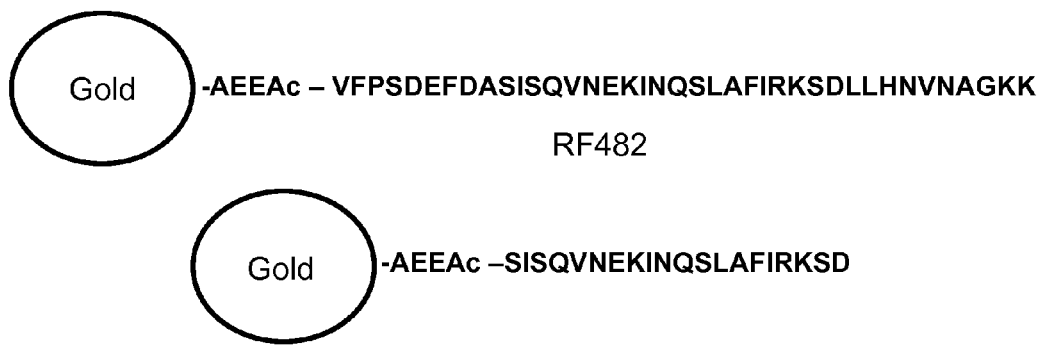
FIG. 6 presents an illustration of the anti-RSV-F peptides RF482 and RF491 bound to carboxylated gold nanoparticles.

While the following description details the preferred embodiments of the present invention, it is to be understood that the invention is not limited in its application to the details of construction and arrangement of the parts illustrated in the accompanying figures, since the invention is capable of other embodiments and of being practiced in various ways.

The peptides of the present invention are derived from peptide sequences identified in the human RSV fusion protein precursor F0. F0 is the precursor protein that is cleaved at two furin cleavage sites to yield the fully functional F1+F2 disulfide-linked dimer. Heptad repeats HR1 and HR2 form alpha-helical structures critical for completing membrane fusion. The RSV fusion protein precursor, F0, is cleaved twice, releasing a 27 amino acid peptide and the F1 and F2 proteins, which are covalently linked by two disulfide bonds. The F1 protein is anchored in the membrane by the transmembrane domain. This cleavage activates the fusion ability of the F protein by releasing the highly hydrophobic "fusion peptide" at the N terminus of F1 (see U.S. Pat. No. 7,700,720).

Nanotechnology has opened up ways to develop newer methods for diagnostics and therapy. Nanoparticles range in size from 1-100 nm and are available in a wide array of materials. Amongst these, the most commonly used nanoparticles include metallic nanoparticles. Gold nanoparticles are one of the most preferred nanoparticles due to their physiochemical properties (Tiwari, P. et al., 2011, Nanomaterials 1(1): 31-63). Gold nanoparticles have been widely studied due to their functionalization capabilities, that is, conjugation with various biomolecules including peptides, proteins, nucleic acids or antibodies. The peptide functionalized gold nanoparticles have gained wide applications for intracellular targeting (Patel, P. C., D. A. Giljohann, et al., 2008, PNAS 105(45): 17222-17226). It is known that gold nanoparticles can be coated with a self-assembled monolayer of compounds containing carboxylic functions. However, these types of gold nanoparticles are known to be useful only for fixing directly to keratin fibers, such as human hair (see U.S. Pat. No. 7,186,274).

Figures 1, 2:
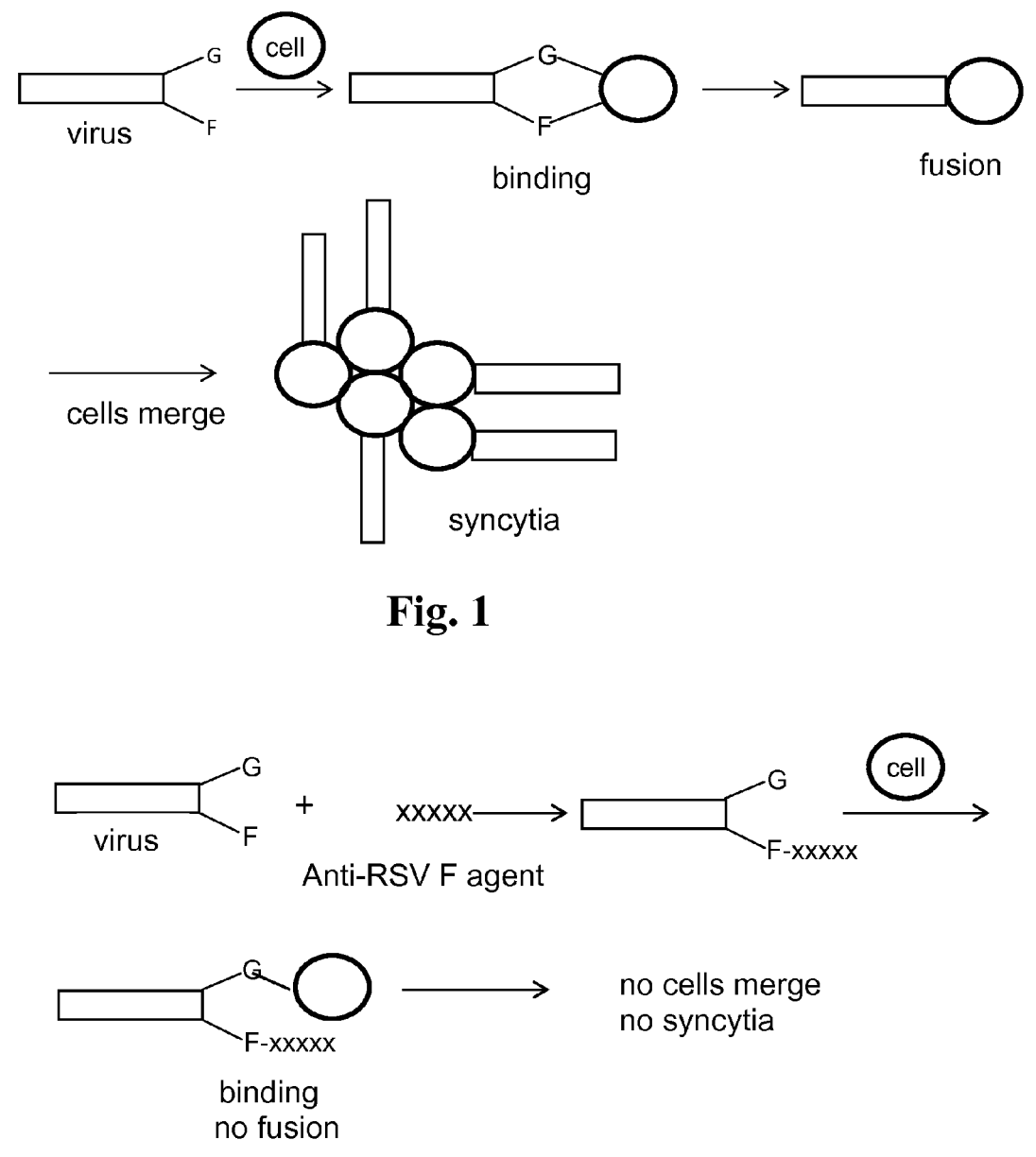

FIG. 1 presents a schematic illustration of the binding and fusion of the human respiratory syncytial virus (RSV) to cells to cause infection of the cells. The RSV has two sites, a G protein (G) and an F protein (F). The G protein functions to bind the virus to the cell. The F protein functions to fuse the virus to the cell once the cell membrane comes into contact with the virus. Once fusion occurs, the cells are induced to merge together and form syncytia. Other paramyxoviruses and HIV viruses also cause infection following a similar mechanism. During infection, viral fusion proteins used by the virus to enter the cell are transported to the cell surface where they can cause the host cell membrane to fuse with neighboring cells. HIV infects CD4+ T cells and makes the cell produce viral proteins, including fusion proteins. Then, the cell begins to display surface HIV glycoproteins, which are antigenic. Normally, a cytotoxic T cell will immediately come to "inject" lymphotoxins, such as perforin or granzyme, that will kill the infected T helper cell. However, if there are nearby T helper cells, the gp41 HIV receptors displayed on the surface of the T helper cell will bind to other similar lymphocytes. This makes dozens of T helper cells fuse cell membranes into a giant, nonfunctional syncytium, which allows the HIV virion to kill many T helper cells by infecting only one.

FIG. 2 presents a schematic illustration of the inhibition of RSV fusion to the cell by binding of an anti-RSV-F agent (xxxxx) to the RSV F protein (F). RF482, carboxylated nanoparticles, and RF482 conjugated to carboxylated nanoparticles of the present invention are anti-RSV-F agents. Fusion inhibitor peptides have been studied previously in other paramyxoviruses including parainfluenza virus type 3 (Pastey et al 2000, Nat. Med. 6(1), 35-40), Henipavirus (Bossart et al, 2005, Virol. J., 2:57) and metapneumovirus (Miller et al 2006, J. Virol. 81:1, 141-149). These fusion inhibitors have been shown to interfere with the 6 helix bundle of the fusion protein, which is highly conserved among the Paramyxoviridae family.

FIG. 3 shows the amino acid regions of the RSV fusion protein precursor F0 from which the two peptides RF482 (SEQ ID NO.: 1) and RF491 (SEQ ID NO.: 2) are derived. The amino acid sequences are shown in this figure. These amino acids were synthesized by methods well known in the art. The characterization of RF482 and RF491 were obtained using Prot Param software from Swiss Prot. The results are shown in Table 1. FIG. 4 provides the Swiss model of RF482 as predicted using ProtParam. FIG. 5 shows the predicted interaction of RF482 with human RSV F using Hex server (protein docking software).

groups. In this regard, H-AEEAc is regarded as linked to the peptide. These peptides were lyophilized and stored at minus 80° C. until needed. The H-AEEAc-RF482 peptide is shown as H-AEEAc-VFPSDEFDASISQVNEKINQSLAFIRKS-DLLHNVNAGKK. The H-AEEAc-RF491 is shown as H-AEEAc-SISQVNEKINQSLAFIRKSD. The H-AEEAc linked to the peptides is used to attach or conjugate the peptide to the carboxylated gold nanoparticles, as illustrated in FIG. 6. The gold nanoparticles were obtained from Nanopartz™ Inc. (Loveland, Colo.). The gold nanoparticles are made of gold salts and have a carboxyl polymer coating. This coating has carboxyl groups (—COOH) available for the conjugation of a wide variety of biomolecules, particularly peptides. The carboxyl groups of the carboxylated gold nanoparticles facilitate the conjugation of the H-AEEAc-RF482 and the H-AEEAc-RF491 peptides to the carboxylated gold nanoparticles by means of the H-AEEAc moiety (linker) of the peptides. The properties of the carboxylated gold nanoparticles are shown in Table 2.

TABLE 2

| Conjugation | Carboxyl Polymer |
| --- | --- |
| Diameter | 13 nm |
| SPR peak | 521 nm |
| pH | 7 |
| Zeta potential | −20 mV |
| Molar extinction coefficient M-1cm-1 | 2.45E+08 |

Method for Conjugation of H-AEEAc-Peptides to Carboxylated Gold Nanoparticles

The carboxylated gold nanoparticles were conjugated with H-AEEAc-RF482 or H-AEEAc-RF491. All of the components were brought to room temperature. A stock aqueous solution was made of water and carboxylated gold nanoparticles at a concentration of 862 nM, relative to the content of gold salts. Stock aqueous solutions were made of the H-AEEAc-peptides, 229 µM (1 mg/ml in water) for H-AEEAc-RF482 peptide and 439 µM (1 mg/ml in water) for

TABLE 1

| Peptide | RF482 | RF491 |
| --- | --- | --- |
| Sequence | VFPSDEFDASISQVNEKIN QSLAFIRKSDLLHNVNAGKK | SISQVNEKINQSLAFIRKSD |
| No. of amino acids: | 39 | 20 |
| Molecular weight: | 4361.8 | 2277.5 |
| Theoretical PI: | 4.95 | 8.31 |
| Net charge | −2 (acidic) | +1 (basic) |
| Atomic composition: formula: | $C_{192}H_{303}N_{53}O_{63}$ | $C_{98}H_{165}N_{29}O_{33}$ |
| Total no. of atoms: | 611 | 325 |

Peptides RF482 and RF491 were also synthesized with an N terminal addition of [(2-amino-ethoxy)-ethoxy]-acetic acid (H-AEEAc) by Bachem Americas Inc. The chemical structure of H-AEEAc is:

$$H_2N\text{—}\diagup\diagdown\text{—}O\text{—}\diagup\diagdown\text{—}O\text{—}\diagup\diagdown\text{—}C(=O)\text{—}OH$$

The carboxyl group of H-AEEAc was reacted with the terminal amine of the peptide to form a peptide bond by methods well known in the art. The 2-amino group of H-AEEAc remains free to form peptide bonds with other carboxyl H-AEEAc-RF491 peptide. 5 ml of a 5 nM concentration of the carboxylated gold nanoparticle solution was placed in a tube and vortexed for 5 seconds. Then a H-AEEAc peptide (390 µl of RF-482 or 207 µl of RF491) was added to these carboxylated gold nanoparticles to give a final H-AEEAc-peptide concentration of 17 µM. This mixture of carboxylated gold nanoparticles and H-AEEAc-peptide was then vortexed for about 1 minute. After this, 25 µl of 1-ethyl-3-(3-dimethylaminopropyl) carbodiimide (EDC) solution (2 mg/ml in water, preferably deionized water) was immediately added to this mixture with stirring, thereby conjugating the H-AEEAc-peptide to the carboxylated gold nanoparticles. 6 to 10 peptide molecules were conjugated to each carboxylated gold nanoparticle. This mixture was then vortexed for 1 hour at room temperature. The mixture was then centrifuged in a microcentrifuge at 14,000 rpm for 45 minutes to obtain a pellet. The supernatant was removed and the pellet was suspended in 5 mL of water, preferably sterile deionized water. Preferably, this process was repeated twice. The final pellet was resuspended in 5 mL of water, preferably sterile deionized water, and sonicated. The carboxylated gold nanoparticles conjugated with the anti-RSV peptide were then used for RSV inhibition experiments. Carboxylated gold nanoparticles alone (i.e., with no peptides or any other substances conjugated thereto) were used as a control solution. In addition, the carboxylated gold nanoparticles conjugated with the RF-482 peptide and the carboxylated gold nanoparticles conjugated with the RF-491 peptide were mixed, preferably in an equimolar ratio, (4 nM final concentration) and were also used for RSV inhibition experiments.

Figure 7:
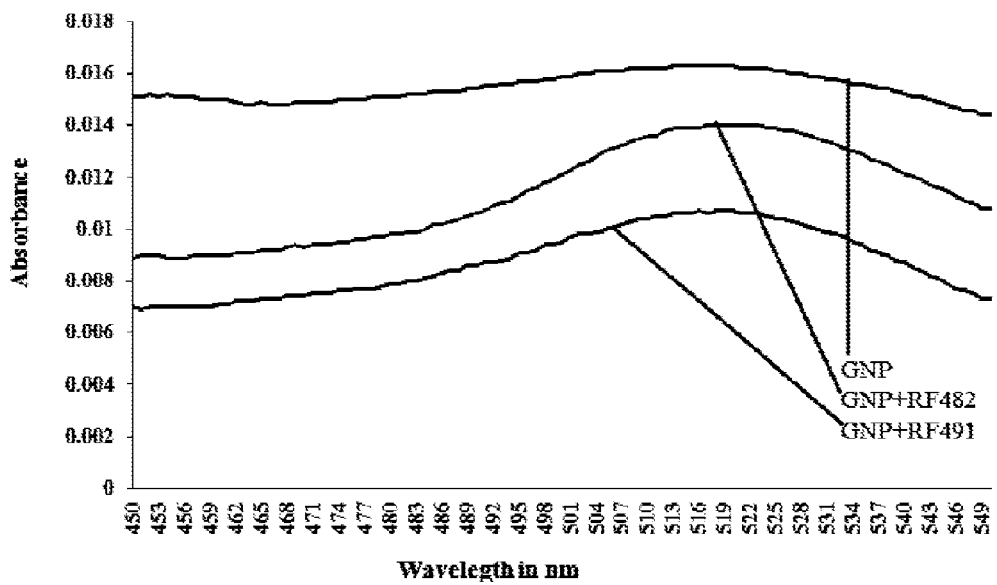
FIG. 7 presents results of UV-Vis spectroscopy of carboxylated gold nanoparticles (GNP) and carboxylated gold nanoparticles conjugated with the RF482 and RF491 peptides.

To ensure successful conjugation of the peptides to the carboxylated gold nanoparticles, UV-Vis spectra was recorded from 450-550 nm. Shift in the surface plasmon resonance (SPR) was used as a measure of conjugation of gold nanoparticles. The results of the UV-Vis spectral analysis are shown in FIG. 7 wherein carboxylated gold nanoparticles are abbreviated as GNP.

Figure 8:
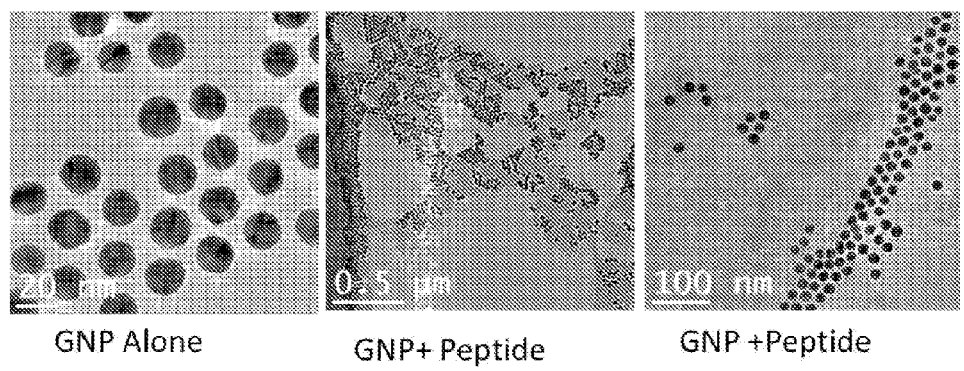
FIG. 8 shows transmission electron microscopy (TEM) images of the carboxylated gold nanoparticles conjugated with peptide.

Further confirmation of conjugation of the peptides to the carboxylated gold nanoparticles was performed by transmission electron microscopy (TEM). The results are shown in FIG. 8. A bright hallow of peptide can be observed around the gold nanoparticles when conjugated with the peptide(s). The carboxylated gold nanoparticles remain spherical after conjugation.

Biological Assays

Figure 9A:
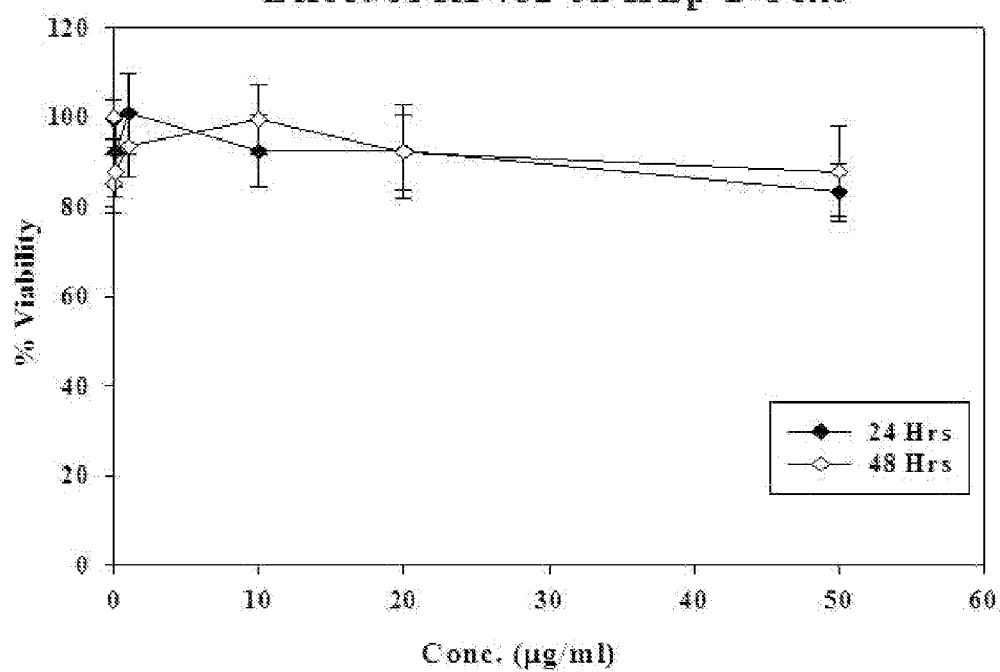
FIGS. 9a and 9b present results of the effect of RF482 and RF491 on the viability of HEp-2 cells.
Figure 9B:
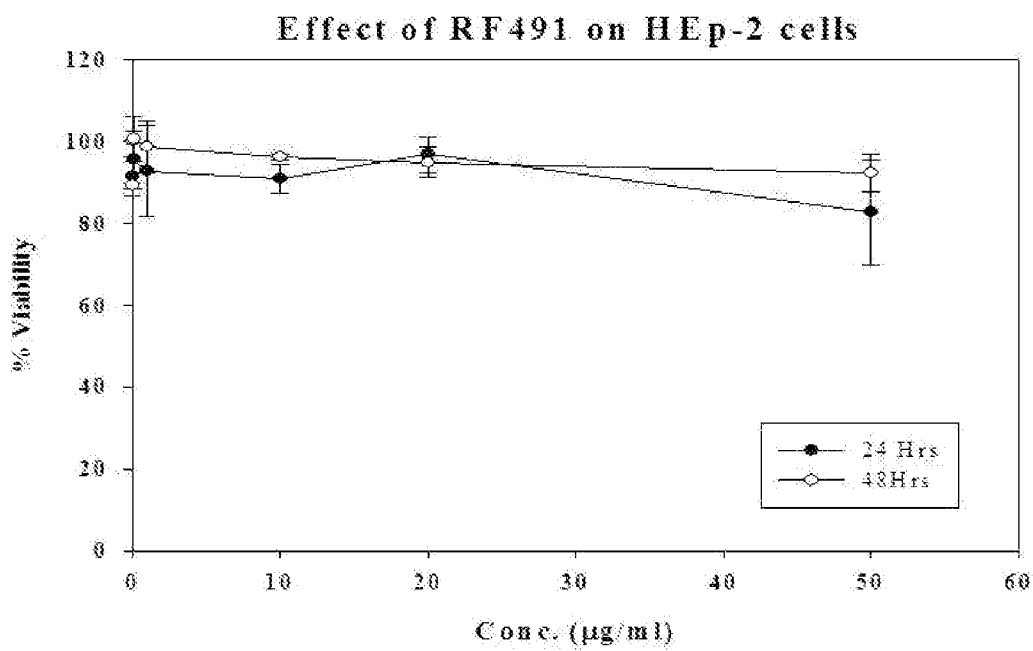
Figure 10A:
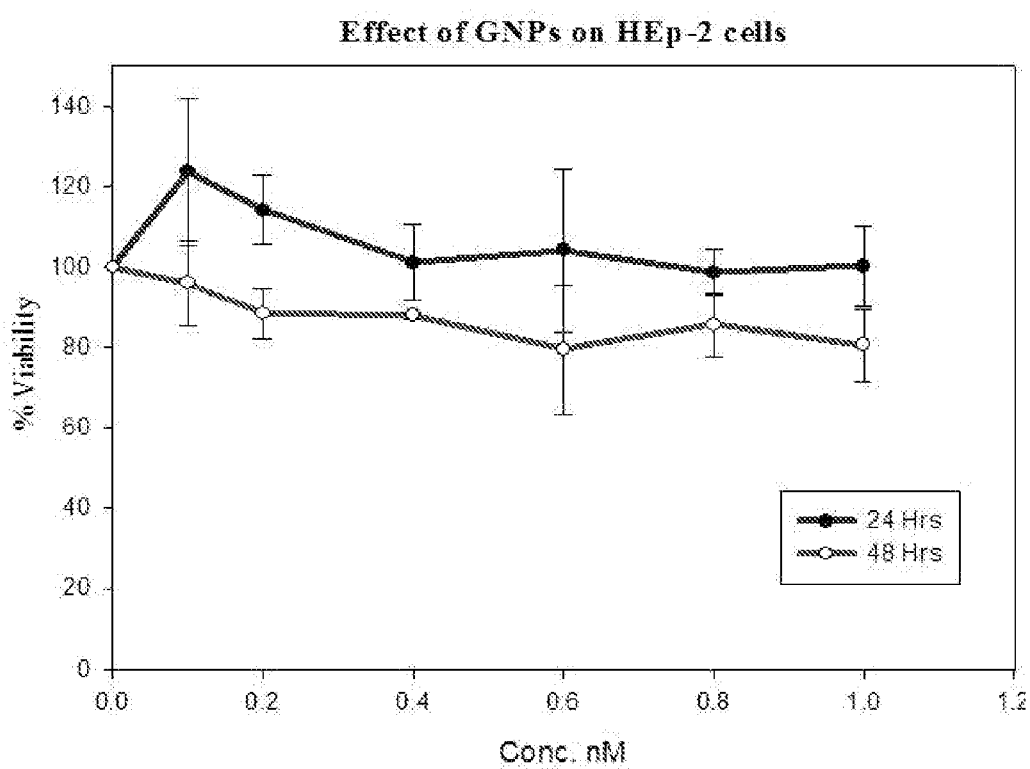
FIGS. 10a, 10b, and 10c present results of the effect of carboxylated gold nanoparticles and carboxylated gold nanoparticles conjugated with the peptides RF482 and RF491 peptides on the viability of HEp-2 cells.
Figure 10B:
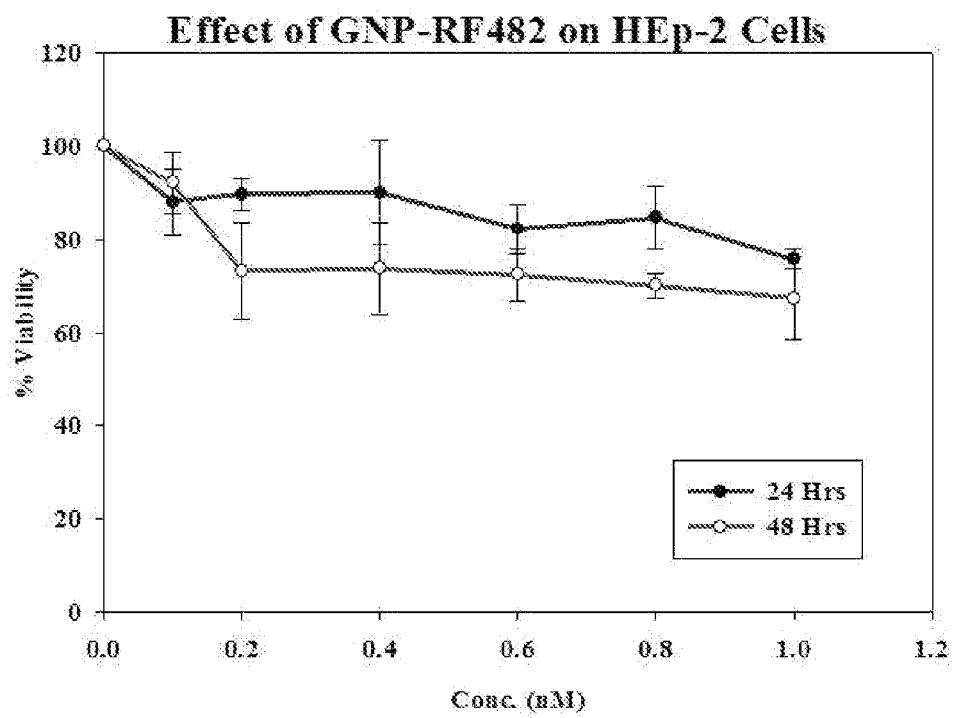
Figure 10C:
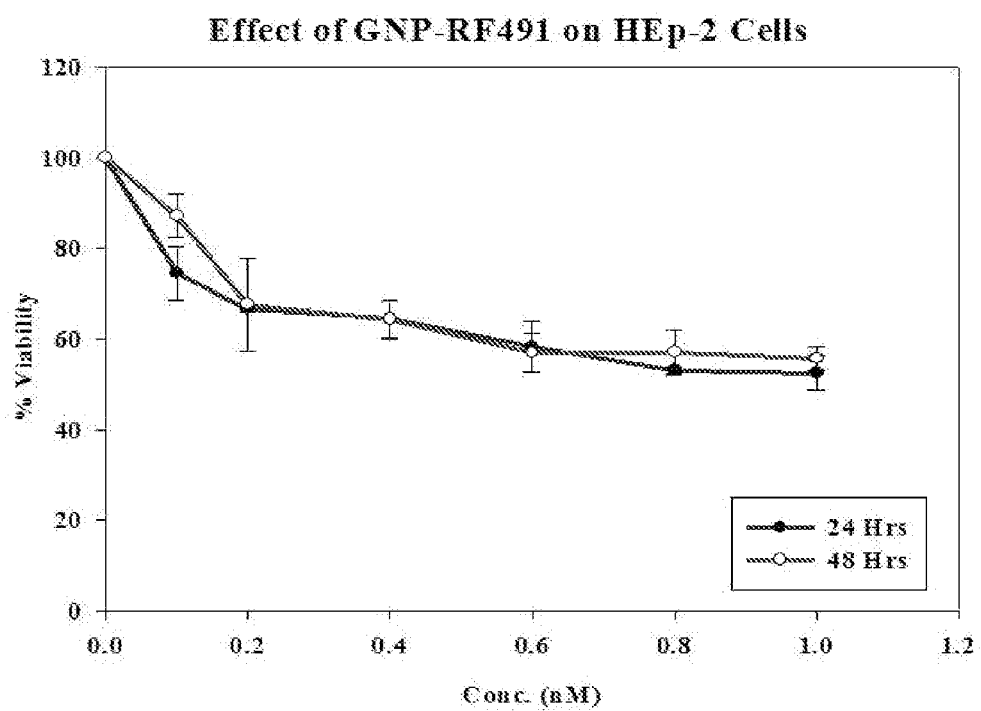

The peptides and carboxylated gold nanoparticles were tested for cytotoxic effects on human epidermoid cancer (HEp-2) cells. Cell viability was assessed by measuring cell concentration of a tetrazolium salt (3-(4,5 dimethyl-2-yl)-5-(3-carboxy-methoxyphenyl)-2-(4-sulfophenyl)-2H-tetrazolium) (MTT). If cells are viable the mitochondria will reduce the MTT. The cells were grown overnight in minimal essential medium (MEM) supplemented with L-glutamine, Penicillin, streptomycin, and kanamycin. 2.7×105 cells/well in 100 μl were seeded into 96-well plates in MEM. Cells were allowed to grow overnight in an incubator at 37° C., with a 5% $CO_2$ humidified atmosphere, until the carboxylated gold nanoparticles were added. After overnight incubation, media from the 96 well plates were replaced with the serial dilutions of RF482, RF491, carboxylated gold nanoparticles (GNP), carboxylated gold nanoparticles conjugated with RF482 (GNP-RF482), or carboxylated gold nanoparticles conjugated with RF491 (GNP-RF491) in MEM-10. Treated cells were further incubated at 37° C., 5% $CO_2$ for 24, and 48 hours. At the end of the corresponding incubation time, 15 μl of MTT dye was added into each well and the plates were allowed to incubate for the next 4 hours in the dark. The reaction was then stopped with 100 μl of stop solution. The absorbance of the media was measured at 570 nm on a TECAN Sunrise enzyme-linked immunosorbent assay plate reader (TECAN, US Inc., Durham, N.C., USA). Non-treated cells in growth media were used as a control. The results with the RF482 and RF491 peptides are shown in FIGS. 9a and 9b. The peptides had no significant effect on cell viability at concentrations up to 50 μg/ml. The effects of carboxylated gold nanoparticles are shown in FIGS. 10a, 10b, and 10c. The carboxylated gold nanoparticles alone (GNP) had no significant effect on cell viability at concentrations up to 1 nM. Carboxylated gold nanoparticles conjugated with RF482 (GNP-RF482) reduced cell viability about 30% at concentrations up to 1 nM. Carboxylated gold nanoparticles conjugated with RF491 (GNP-RF491) reduced cell viability about 40% at concentrations up to 1 nM.

Figure 11A:
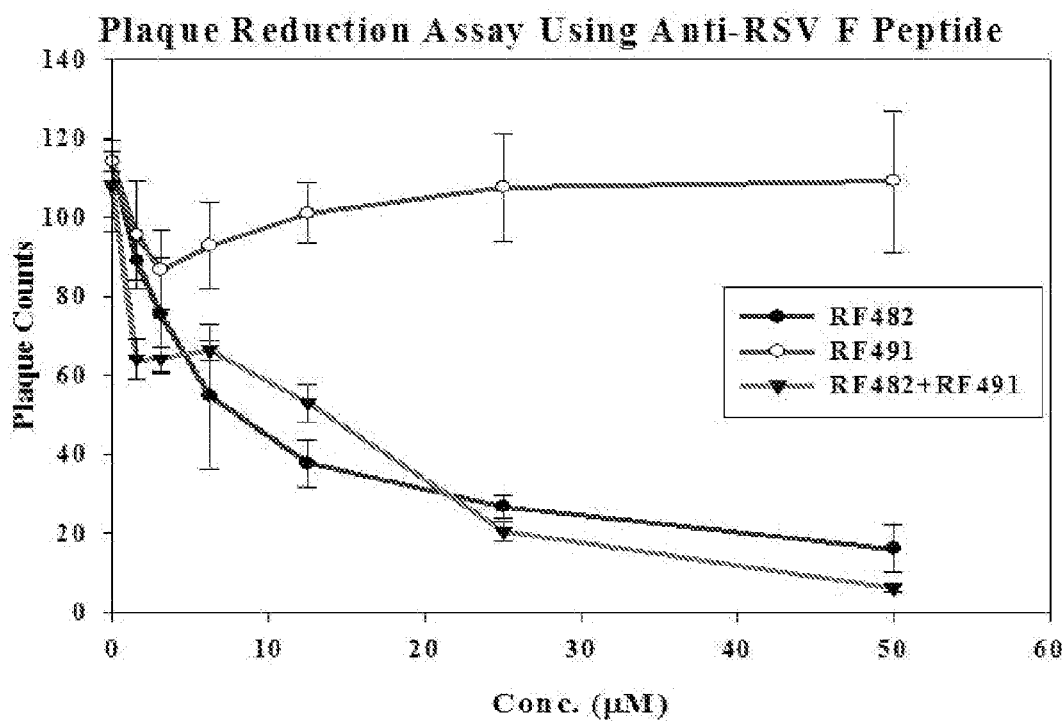
FIGS. 11a and 11b show the inhibition of RSV infection in HEp-2 cells with RF482, RF491, or carboxylated gold nanoparticles or carboxylated gold nanoparticles conjugated with the RF482 and RF491 peptides.
Figure 11B:
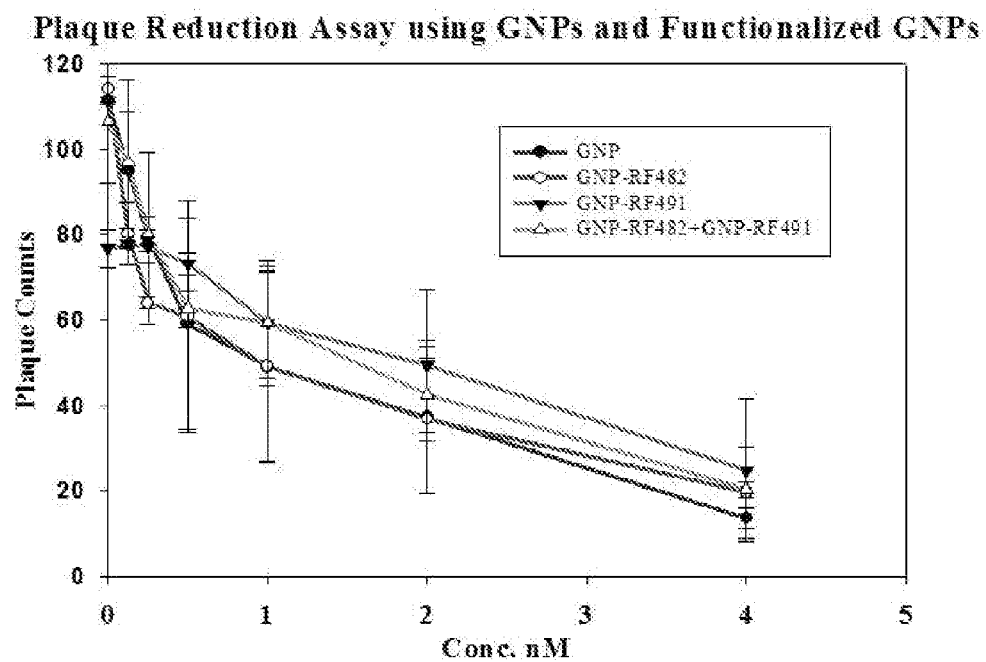

The peptides and carboxylated gold nanoparticles were tested for inhibition (antifusogenic activity) of RSV infection in HEp-2 cells. HEp-2 cells were grown in MEM in 12 well plates. 100 plaque forming Units (PFUs) of RSV, mixed with 1) RF482, 2) RF491, 3) RF482+RF491, 4) carboxylated gold nanoparticles (GNP), 5) carboxylated gold nanoparticles conjugated with RF482 (GNP-RF482), 6) carboxylated gold nanoparticles conjugated with RF491 (GNP-RF491), or 7) a mixture of carboxylated gold nanoparticles conjugated with RF491 and RF492 (GNP-RF482+GNP-RF491), were made up to a final volume of 100 μl with MEM and incubated at RT for 30 minutes. Final concentrations of the peptides used were 50 μM, 25 μM, 12.5 μM, 6.25 μM and 3.125 μM. The concentration of carboxylated gold nanoparticles ranged from 0.125 nM to 4 nM. The mixtures were assessed for viral titers. The mixtures were then added to HEp-2 cells maintained in 12 well plates. After incubating the cells with RSV for an hour at 37° C., methylcellulose overlay containing DMEM (Dulbecco's Minimal Essential Medium) and FBS (Fetal Bovine Serum) (2%) (volume/volume) was added to cells to maintain the virus number in the overlay and incubated for 72 hours. At the end of the incubation period, the methylcellulose layer was removed and cell monolayer was stained with crystal violet for the enumeration of the RSV plaques. Results were expressed in plaque forming units (PFUs)/ml. The results for inhibition (antifusogenic activity) of RSV infection are shown in FIGS. 11a and 11b. RF482 and RF482+RF491 reduced plaque counts by about 80% to 90% at 50 μM concentrations. RF491 was not effective in reducing plaque counts. The carboxylated gold nanoparticles, alone or conjugated with the peptides, reduced plaque counts by about 75% to 85% at 4 nM concentrations.

Prophylactic and Therapeutic Uses of Anti-RSV-F Peptides, Carboxylated Gold Nanoparticles, and Carboxylated Gold Nanoparticles Conjugated with Anti-RSV-F Peptides Anti-RSV agents of the present invention (RF482, carboxylated gold nanoparticles, and carboxylated gold nanoparticles conjugated with RF482, RF491, or both) may be used locally or systemically in the body as therapeutics. They may also be advantageously utilized in combination with one or more drugs used to treat RSV infection such as, for example anti-viral agents. They may be administered alone or in combination with other types of treatments (e.g., hormonal therapy, immunotherapy, and anti-inflammatory agents). Therapeutic or pharmaceutical compositions comprising anti-RSV agents of the present invention are administered to a mammal, preferably a human, to treat, prevent or ameliorate one or more symptoms associated with RSV infection. They are also administered to a human with cystic fibrosis, bronchopulmonary dysplasia, congenital heart disease, congenital immunodeficiency or acquired immunodeficiency, or to a human who has had a bone marrow transplant to treat, prevent or ameliorate one or more symptoms associated with RSV infection. They are also administered to a human infant, preferably a human infant born prematurely or a human infant at risk of hospitalization for RSV infection to treat, prevent or ameliorate one or more symptoms associated with RSV infection, and are administered to the elderly or people in nursing homes or rehabilitation centers. In view of the fact that the anti-RSV agents of the present invention are effective in preventing fusion of RSV to target cells, they are also useful for the treatment of infections produced by parainfluenza viruses of Paramyxoviridae family and by the human immunodeficiency virus (HIV).

Methods of Administration

The invention provides methods of treatment, prophylaxis, and amelioration of one or more symptoms associated with RSV infection by administrating to a subject compositions of the anti-RSV agents of the present invention, or a pharmaceutical composition comprising the anti-RSV agents of the present invention. In a preferred aspect, the subject the anti-RSV agents of the present invention are substantially purified (i.e., substantially free from substances that limit its effect or produce undesired side-effects). The subject is preferably a mammal such as non-primate (e.g., cows, pigs, horses, cats, dogs, rats etc.) and a primate (e.g., monkey such as a cynomolgous monkey and a human). In a preferred embodiment, the subject is a human. In another preferred embodiment, the subject is a human infant or a human infant born prematurely. In another embodiment, the subject is a human with cystic fibrosis, bronchopulmonary dysplasia, congenital heart disease, congenital immunodeficiency or acquired immunodeficiency, a human who has had a bone marrow transplant, or an elderly human.

Various delivery systems are known and can be used to subject the anti-RSV agents of the present invention e.g., encapsulation in liposomes, microparticles, and microcapsules. Methods of administering the compositions of the anti-RSV agents of the present invention include but are not limited to, parenteral administration (e.g., intradermal, intramuscular, intraperitoneal, intravenous and subcutaneous), epidural, and mucosal (e.g., intranasal and oral routes). The pharmaceutical compositions of the anti-RSV agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. The compositions and pharmaceutical compositions may be administered locally to the area in need of treatment; this may be achieved by, for example, local infusion, by injection, or by means of an implant, the implant being of a porous, non-porous, or gelatinous material, including membranes, such as sialastic membranes, or fibers.

The compositions and pharmaceutical compositions of the invention can be delivered in a controlled release or sustained release system. For example, a pump may be used to achieve controlled or sustained release. Polymeric materials can be used to achieve controlled or sustained release. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation is inert, free of leachable impurities, stable on storage, sterile, and biodegradable. A controlled or sustained release system can be placed in proximity of the therapeutic target, i.e., the lungs.

Pharmaceutical compositions comprise a prophylactically or therapeutically effective amount of the anti-RSV agents and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc.

Intravenous pharmaceutical compositions of the invention are formulated in accordance with routine procedures as a pharmaceutical composition adapted for intravenous administration to human beings. Typically, compositions for intravenous administration are solutions in sterile isotonic aqueous buffer. The composition may also include a solubilizing agent and a local anesthetic such as lignocaine to ease pain at the site of the injection.

The amount of the composition of the invention which will be effective in the treatment, prevention, or amelioration of one or more symptoms associated with a RSV infection, can be determined by standard clinical techniques. For example, the dosage of the composition which will be effective in the treatment, prevention or amelioration of one or more symptoms associated with a RSV infection can be determined by administering the composition to a rat, measuring the RSV titer after challenging the rat with $10^5$ pfu of RSV and comparing the RSV titer to that obtain for a rat not administered the composition. Accordingly, a dosage that results in a 2 log decrease or a 99% reduction in RSV titer in the rat challenged with $10^5$ pfu of RSV relative to the rat challenged with $10^5$ pfu of RSV but not administered the composition is the dosage of the composition that can be administered to a human for the treatment, prevention or amelioration of symptoms associated with RSV infection. In addition, in vitro assays may optionally be employed to help identify optimal dosage ranges.

It will be understood that various changes in the details, materials, and arrangements of the parts which have been described and illustrated above in order to explain the nature of this invention may be made by those skilled in the art without departing from the principle and scope of the invention as recited in the following claims. Those skilled in the art will recognize, or be able to ascertain using no more than routine experimentation, many equivalents to the specific embodiments of the invention described herein. Such equivalents are intended to be encompassed by the following claims.

The invention claimed is:

1. An anti-respiratory syncytial virus (RSV) peptide comprising the amino acid sequence consisting of VFPSDEFDASISQVNEKINQSLAFIRKSDLLHNVNAGKK (SEQ ID No: 1).

2. The anti-RSV peptide of claim 1 wherein said anti-RSV peptide is linked to [(2-amino-ethoxy)-ethoxy]-acetic acid at the N-terminal of said anti-RSV peptide.

3. The anti-RSV peptide of claim 2 wherein said anti-RSV peptide is conjugated to a carboxylated gold nanoparticle at the 2-amino end of the [(2-amino-ethoxy)-ethoxy]-acetic acid linked at the N-terminal of said anti-RSV peptide.

4. A pharmaceutical composition comprising the anti-RSV peptide of claim 1 and one or more pharmaceutically acceptable carriers selected from the group consisting of poly(2-hydroxy ethyl methacrylate), poly(methyl methacrylate), poly(acrylic acid), poly(ethylene-co-vinyl acetate), poly(methacrylic acid), polyglycolides, polyanhydrides, poly(N-vinyl pyrrolidone), poly(vinyl alcohol), polyacrylamide, poly(ethylene glycol), polylactides, poly(lactide-co-glycolides), polyorthoesters, water, peanut oil, soybean oil, mineral oil, sesame oil, saline, aqueous dextrose, glycerol, starch, glucose, lactose, sucrose, gelatin, malt, rice, flour, chalk, silica gel, sodium stearate, glycerol monostearate, talc, sodium chloride, dried skim milk, glycerol, propylene glycol, and ethanol, wherein said pharmaceutical composition inhibits infection by a respiratory syncytial virus when administered to a subject in need thereof.

5. A pharmaceutical composition comprising the anti-RSV peptide of claim 3 and one or more pharmaceutically acceptable carriers selected from the group consisting of poly(2-hydroxy ethyl methacrylate), poly(methyl methacrylate), poly(acrylic acid), poly(ethylene-co-vinyl acetate), poly(methacrylic acid), polyglycolides, polyanhydrides, poly(N-vinyl pyrrolidone), polyvinyl alcohol), polyacrylamide, poly(ethylene glycol), polylactides, poly(lactide-co-glycolides), polyorthoesters, water, peanut oil, soybean oil, mineral oil, sesame oil, saline, aqueous dextrose, glycerol, starch, glucose, lactose, sucrose, gelatin, malt, rice, flour, chalk, silica gel, sodium stearate, glycerol monostearate, talc, sodium chloride, dried skim milk, glycerol, propylene glycol, and ethanol, wherein said pharmaceutical composition inhibits infection by a respiratory syncytial virus when administered to a subject in need thereof.

6. An anti-respiratory syncytial virus (RSV) peptide comprising the amino acid sequence consisting of SISQVNEKINQSLAFIRKSD (SEQ ID No: 2), wherein said anti-RSV peptide is linked to [(2-amino-ethoxy)-ethoxy]-acetic acid at the N-terminal of said anti-RSV peptide, and wherein said anti-RSV peptide is conjugated to a carboxylated gold nanoparticle at the 2-amino end of the [(2-amino-ethoxy)-ethoxy]-acetic acid linked at the N-terminal of said anti-RSV peptide.

7. A pharmaceutical composition comprising the anti-RSV peptide of claim 6 and one or more pharmaceutically acceptable carriers selected from the group consisting of poly(-hydroxy ethyl methacrylate), poly(methyl methacrylate), poly(acrylic acid), poly(ethylene-co-vinyl acetate), poly(methacrylic acid), polyglycolides, polyanhydrides, poly(N-vinyl pyrrolidone), poly(vinyl alcohol), polyacrylamide, poly(ethylene glycol), polylactides, poly(lactide-co-glycolides), polyorthoesters, water, peanut oil, soybean oil, mineral oil, sesame oil, saline, aqueous dextrose, glycerol, starch, glucose, lactose, sucrose, gelatin, malt, rice, flour, chalk, silica gel, sodium stearate, glycerol monostearate, talc, sodium chloride, dried skim milk, glycerol, propylene glycol, and ethanol, wherein said pharmaceutical composition inhibits infection by a respiratory syncytial virus when administered to a subject in need thereof.

8. Anti-respiratory syncytial virus (RSV) carboxylated gold nanoparticles, comprising carboxylated gold nanoparticles conjugated with the peptide of SEQ ID No: 1 or with the peptide of SEQ ID No: 2, wherein said peptides are linked to [(2-amino-ethoxy)-ethoxy]-acetic acid.

9. The anti-RSV carboxylated gold nanoparticles of claim 8 wherein said carboxylated gold nanoparticles have a carboxyl polymer coating and a mean diameter of 13 nm.

10. The anti-RSV carboxylated gold nanoparticles of claim 8 wherein 6 to 10 peptide molecules are conjugated to each of said carboxylated gold nanoparticles.

11. Anti-respiratory syncytial virus (RSV) carboxylated gold nanoparticles, comprising carboxylated gold nanoparticles conjugated with the peptide of SEQ ID No: 1 or with the peptide of SEQ ID No: 2, wherein said peptides are linked to [(2-amino-ethoxy)-ethoxy]-acetic acid, wherein said carboxylated gold nanoparticles have a carboxyl polymer coating and a mean diameter of 13 nm and wherein 6 to 10 peptide molecules are conjugated to each of said carboxylated gold nanoparticles.

12. A pharmaceutical composition comprising said anti-RSV carboxylated gold nanoparticles of claim 11 and one or more pharmaceutically acceptable carriers selected from the group consisting of poly(2-hydroxy ethyl methacrylate), poly (methyl methacrylate), poly(acrylic acid), poly(ethylene-co-vinyl acetate), poly(methacrylic acid), polyglycolides, polyanhydrides, poly(N-vinyl pyrrolidone), poly(vinyl alcohol), polyacrylamide, poly(ethylene glycol), polylactides, poly (lactide-co-glycolides), polyorthoesters, water, peanut oil, soybean oil, mineral oil, sesame oil, saline, aqueous dextrose, glycerol, starch, glucose, lactose, sucrose, gelatin, malt, rice, flour, chalk, silica gel, sodium stearate, glycerol monostearate, talc, sodium chloride, dried skim milk, glycerol, propylene glycol, and ethanol, wherein said pharmaceutical composition inhibits infection by a respiratory syncytial virus when administered to a subject in need thereof.

* * * * *